United States Patent [19]

Incropera et al.

[11] 3,991,764

[45] Nov. 16, 1976

[54] PLASMA ARC SCALPEL

[75] Inventors: Frank P. Incropera, West Lafayette; William J. Link, Indianapolis, both of Ind.

[73] Assignee: Purdue Research Foundation, West Lafayette, Ind.

[22] Filed: Aug. 13, 1975

[21] Appl. No.: 604,234

Related U.S. Application Data

[63] Continuation of Ser. No. 419,620, Nov. 28, 1973, abandoned.

[52] U.S. Cl. .................. 128/303.1; 219/121 P; 313/231.4; 315/111.2
[51] Int. Cl.² .................................................. A61B 17/36
[58] Field of Search....... 128/303.1, 303.14, 303.17; 204/362, 164; 219/121 P; 313/231.3, 231.4, 231.5; 315/111.2, 111.3

[56] References Cited
UNITED STATES PATENTS

| 3,182,176 | 5/1965 | Bunt et al. | 219/121 P |
| 3,434,476 | 3/1969 | Shaw et al. | 128/303.1 |
| 3,632,951 | 1/1972 | Klasson | 219/121 P |
| 3,858,072 | 12/1974 | Dembovsky | 313/231.4 |

*Primary Examiner*—William E. Kamm
*Attorney, Agent, or Firm*—John R. Nesbitt

[57] ABSTRACT

This disclosure relates to a surgical tool that employs a jet of inert gas passed through a direct current electric arc which imparts thermal energy to the gas jet which is then ejected from a small orifice at a temperature sufficient to simultaneously incise and cauterize living tissue. The tool includes a tool body having a tubular anode therein with said anode having a cathode and cathode assembly therein, said anode and cathode being concentric with respect to one another and spaced from one another. Said tool body also includes a sheath therein between said anode and said tool body so that coolant is caused to flow in separate paths. In addition, a plunger is also provided to move the cathode longitudinally into contact with the anode so that, upon release and retraction of the cathode, an electrical arc is established so that inert gas flowing through said arc is ejected from the tool as a hot plasma.

6 Claims, 3 Drawing Figures

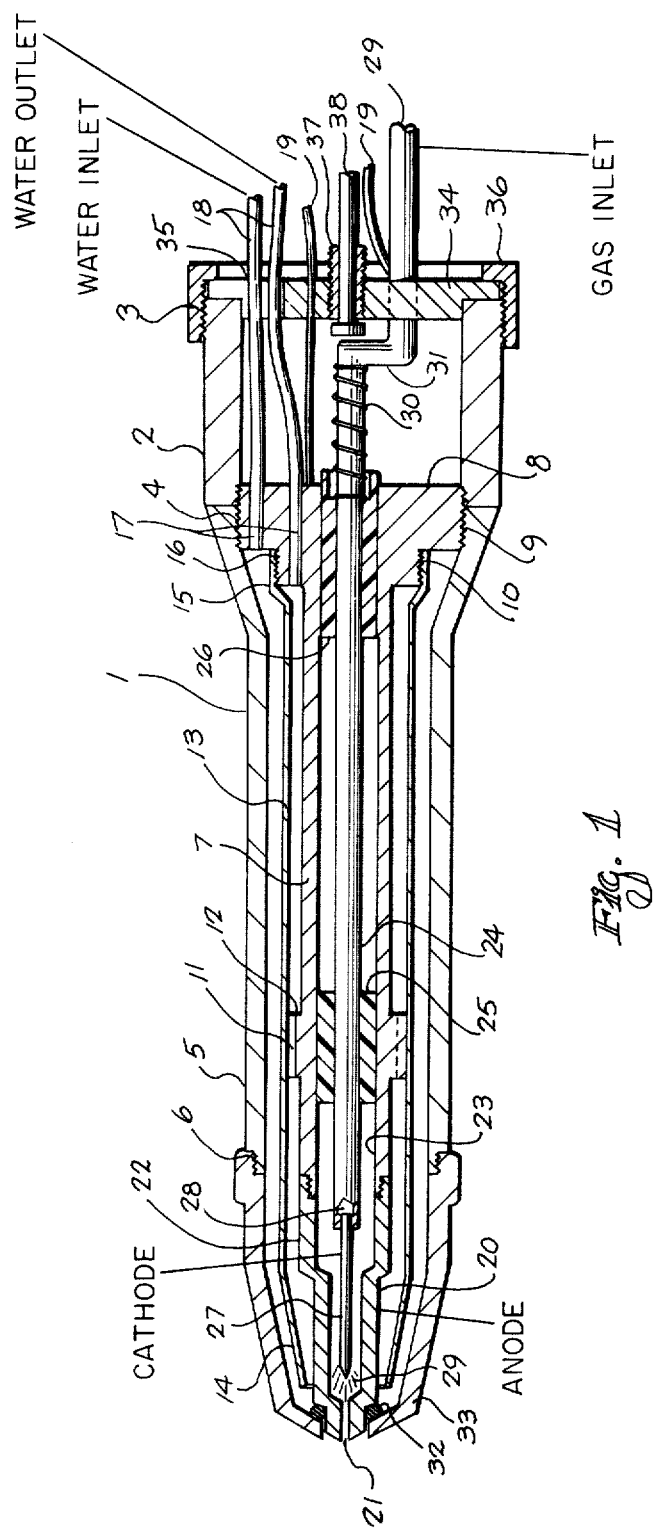

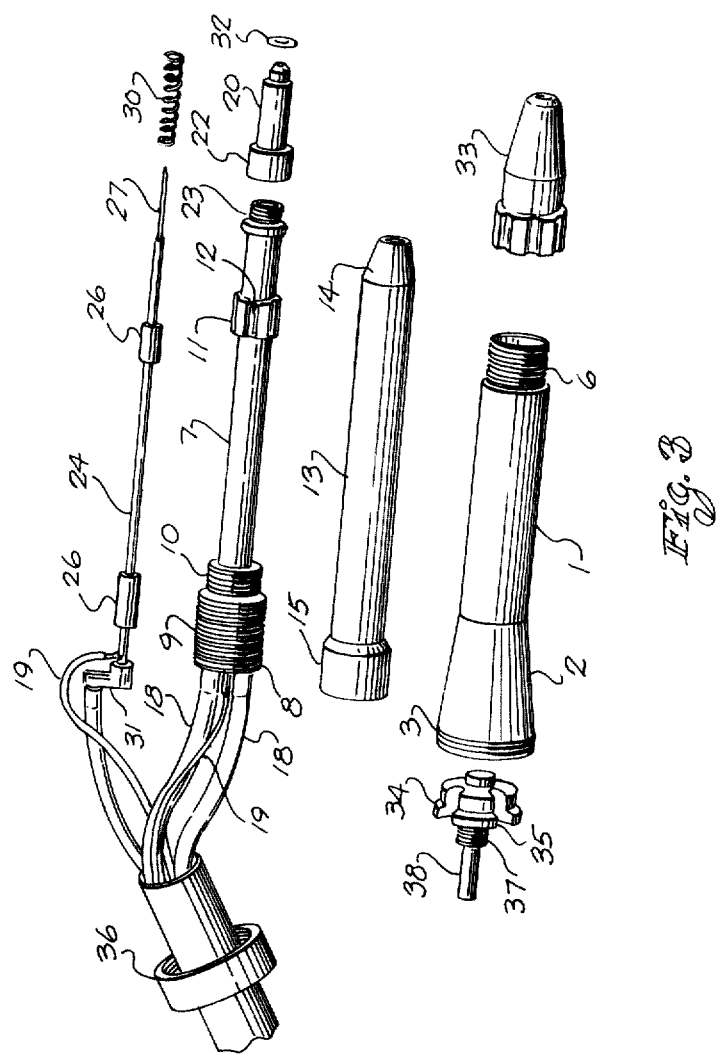
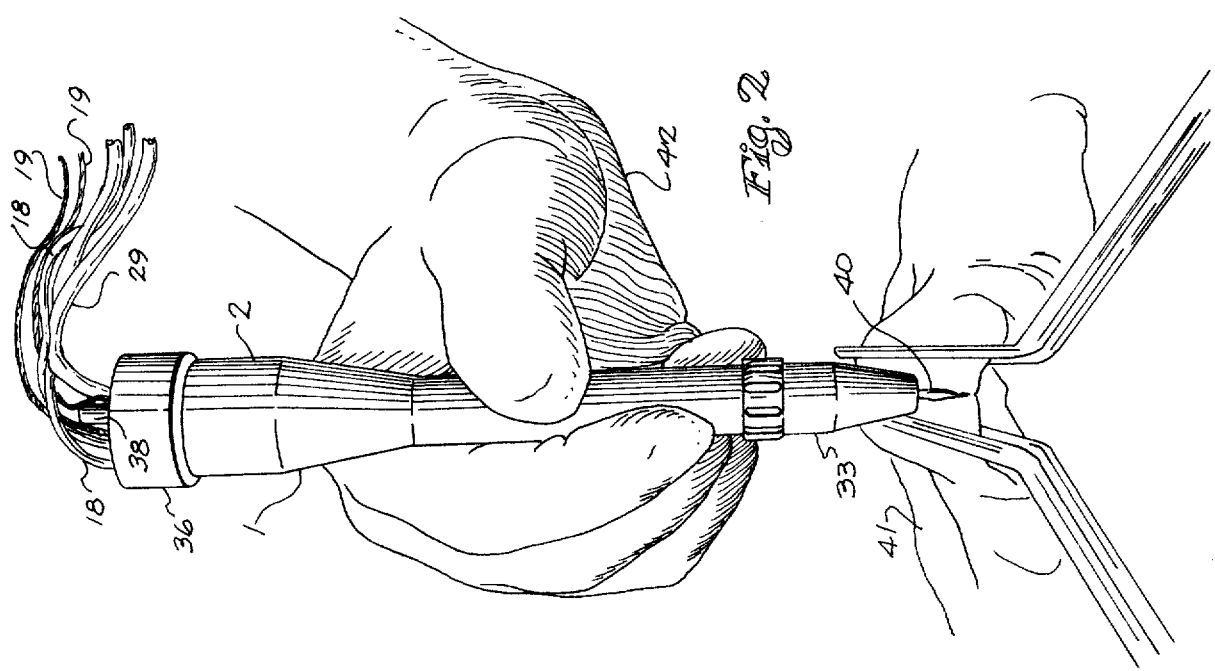

PLASMA ARC SCALPEL

The Government has rights in this invention pursuant to Grant Nos. GK 26586 and GK 3383 awarded by the National Science Foundation.

This is a continuation of application Ser. No. 419,620, filed Nov. 28, 1973 now abandoned.

FIELD OF THE INVENTION

This invention relates to a surgical cutting tool and, more particularly, to a plasma arc scalpel.

BACKGROND OF THE INVENTION

1. The oldest method of controlling surgical bleeding is to ligate (tie-off) bleeding vessels. This approach is excessively time consuming and if the bleeding vessels are numerous (e.g. in highly vascular organs) this method is sometimes ineffective.

2. An electrocautery scalpel (surgical diathermy) is commonly used to cauterize bleeding vessels. This device coagulates vessels by imposing a high voltage, low current signal on the vessels. This device is also used in making incisions, but will not simultaneously cauterize vessels larger than 1 mm in diameter.

3. Since December of 1966 a "Plasma Scalpel" developed by Hogle-Kearns International (H-K) of Salt Lake City, Utah, has been used in experimental animal surgery at the University of Utah Medical Center, Division of Neurosurgery.

The H-K "Plasma Scalpel" uses a radio frequency energy and argon gas to produce a thermal plasma with minimum temperatures above 8,000° Kelvin. The thermal plasma in this case is a gas that has absorbed enough radio frequency energy to become ionized or electrically conductive. This method of plasma generation is further described as an "E Field Plasma."

The plasma, as it emits from the tip of the hand piece, is of small diameter ( .007 of an inch) and with the high temperature gradient upon contact with live tissue a finite area of vaporization occurs, leaving a relatively hemorrhage-free incision. To date, the device has not yet been used on live human tissue. This type of plasma scalpel is further described in The Journal of the American Medical Association, Apr. 29, 1968, Vol 204, No.5.

(4). Laser scalpels are presently being developed to promote "bloodless" incisions. Laser scalpels are still in the developmental stage, have limited maneuverability, and require a considerably higher investment than does the device hereinafter described.

SUMMARY OF THE INVENTION

The operating gas (argon, helium, or a mixture thereof) is passed through a direct current electric arc and is energized by a conversion from electrical to thermal energy. The operating gas, in the form of a high-temperature, ionized plasma gas, subsequently emerges from the scalpel body through a small orifice. The plasma jet thus emerging from the scalpel is utilized to effect the desired simultaneous incision and cauterization in tissue.

The plasma arc scalpel operates continuously in a stable mode, by satisfying the following requirements:

A. Controlled electrical energy is delivered to the device.

B. Operating gas flow is maintained at the desired rate.

C. The electrodes are cooled to maintain the integrity of the tool.

Both the electrosurgical and the "E Field Plasma" devices use radio frequencies to generate the arc or plasma. The electrosurgical unit is especially prone to the production of radio frequency burns at sites other than the incision or cautery. The present devce is entirely free of such burns because it does not employ radio frequencies.

DESCRIPTION OF THE DRAWINGS

FIG. 1 is a cross sectional view of a cooled plasma arc scalpel.

FIG. 2 is a perspective view of the plasma arc scalpel shown in FIG. 1 in operative use.

FIG. 3 is a disassembled view of the plasma arc scalpel.

DETAILED DESCRIPTION OF THE INVENTION

A housing 1 has a flared end 2 that is externally threaded at 3 and internally threaded at 4 and has its other end 5 externally threaded at 6. An anode assembly 7 has one enlarged end 8, said enlarged end having a first externally threaded portion 9 and a second externally threaded portion 10. The anode assembly has an enlarged collar 11 with passages 12, which collar serves to support sheath 13. Sheath 13 has tapered end 14 and an enlarged end 15 having internal threads 16. The enlarged end 8 of the anode assembly has water outlet and inlet passages 17 to which are connected water lines 18. An electrical wire 19 is electrically connected to anode assembly 7. An anode 20 having a fluid passage 21 at one end and an enlarged internally threaded end 22, is adapted to threadably engage the externally threaded end 23 of anode assembly 7. Anode 20 is preferably interchangeable to provide fluid passages of differing sizes to vary cut sizes as desired. A cathode tube 24 is insulatively and slidably mounted in spaced relation inside the anode assembly by means of insulators 25, 26. The cathode 27 is press fitted to cathode tube 24, leaving plasma exit passages 28 to permit inert gas 29 injected into the cathode tube to flow through the electric arc when the device is in operation.

It will be readily apparent that the device is easily assembled by inserting the cathode tube 24 inside the anode assembly 7. A spring 30 is captured between the anode assembly insulator 26 and a bend 31 in the cathode tube. The anode is threadably connected to the anode assembly. The cathode tube assembly is inserted inside housing 1 and a high temperature resistant O-ring 32 effects a watertight seal between the anode 20 and tip cap 33 when the tip is threadably engaged with housing 1. Then an end cap 34 having cutouts 35 for passage therethrough of the water coolant lines 18 and one of the electrical supply wires 19 fits within flared end 2 of housing 1 and is held in place by retainer ring 36, which ring is internally threaded and is received on externally threaded end 2 of housing 1. The other electrical wire 19 is connected to the cathode tube. A plunger guide 37 is inserted through and threadably connected to end cap 34. A plunger 38 is slidably mounted in plunger guide 37 and extends inside the housing into contact with the bent portion 31 of the cathode tube, which bent end is located so as to exert a slight pressure (from left to right as viewed in FIG. 1) against the plunger. The cathode tube is then moveable by depressing the plunger and an electric arc is initiated by advancing the cathode until it contacts the anode and then by releasing pressure on the plunger the cathode retracts to its original position.

The step-by-step procedure for assembling the plasma arc scalpel of this invention is therefore as follows:

1. Anode 20 is threaded onto anode assembly 8.
2. Sheath 13 is threaded onto anode assembly 8.
3. O-ring 32 is placed on anode tip.
4. Tip cap 33 is threaded onto housing 5.
5. Anode assembly 7 with attached sheath 13 is inserted into housing 5 and threadably connected until O-ring 32 makes sealing contact with inside of tip cap 33.
6. Housing 2 is threaded onto anode assembly 7 until sealing relationship with 1 is made.
7. Plunger guide 37 is threaded into end cap 34.
8. Plunger 38 is inserted into plunger guide 37.
9. Cathode tube 24 is inserted into spring 30 until spring contacts bend portion 31.
10. Cathode tube is inserted through spacers 25 and 26.
11. End cap is inserted in housing 2.
12. Retainer ring 36 is threaded onto housing 2.

Water coolant enters the device through one of tubes 18 and flows in a random manner around the outside surface of sheath 13 until it reaches the point of highest temperature at the tip of the anode 20 where it is permitted to contact the anode and then it flows back inside the sheath and over the outside surface of the anode assembly and then through passages 12 and 17 to where it exits via another tube 18.

Inert gas 29 flows into the cathode tube 24 and exits alongside the cathode 27 and passes through the electric arc where it is heated into a hot plasma, the temperature of which is determined by the voltage applied across the anode and cathode, the gap width between the anode and cathode, and the volume flow rate and composition of the operating gas. This hot plasma 40 then exits through aperture 21 where it is directed against the tissue 41 which it is desired to incise and cauterize, the arc scalpel being held, as by hand 42 as shown in FIG. 2. Experiments with a power supply voltage of 150 volts and 15 amperes, providing up to a 30 volt potential between the electrodes, using this device, have shown that vessels up to 5 mm in diameter can be simultaneoulsy incised and cauterized.

What is claimed is:

1. A surgical tool for simultaneously incising and cauterizing live tissue comprising:
    a tool body having exterior and interior portions and a discharge end;
    means for supplying a cool inert gas to said tool body;
    an anode and a cathode carried by said tool body, said anode having a tip portion adjacent to the discharge end of said tool body, and said anode and cathode being relatively movable with respect to one another;
    a cathode carrier tube having a supply inlet near one end portion connected with said means for supplying said cool inert gas and an outlet near the other end portion, said other end portion having said cathode mounted thereon with said inert gas being conducted through said carrier tube and ejected adjacent said cathode and passed through a electrical arc, said gas being then discharged from said tool body through said discharge end thereof as plasma gas for contacting live tissue to be incised and cauterized adjacent to said discharge end of said tool body;
    coolant passage means inside said tool body and extending to the tip portion of said anode to cool the anode including said tip portion;
    electrical means to impress a desired voltage across the anode and cathode means; and
    means to cause momentary movement of the cathode and anode toward contacting relationship to thereby establish an arc therebetween.

2. A surgical tool according to claim 1 in which said coolant passage means provides an annular passage to conduct coolant adjacent the tool body to the hot anode inside the tool and then to return said coolant along a separate annular path adjacent to and radially offset from said annular passage to provide additional anode cooling whereby the tool body remains cool and the coolant heated by the anode continues to cool the anode and does not impart anode heat to the tool body exterior.

3. A surgical tool according to claim 2 in which the annular passage and separate annular path of said coolant passage means are concentric with respect to one another with coolant in said annular passage being conducted therethrough in a direction opposite to the direction in which coolant is conducted through said separate annular path with said cooling of said anode being optimized.

4. A surgical tool according to claim 1 in which said coolant passage means includes a shield tube one end of which terminates adjacent to said cathode so that coolant is directed to said tip portion of said anode for cooling of the same.

5. A surgical tool for simultaneously incising and cauterizing live tissue comprising:
    a tool body;
    a cathode carrier tube having a supply inlet near one end portion and an outlet near the other end portion;
    a cathode secured to said other end portion of said carrier tube so that gas supplied to said supply inlet of said cathode carrier tube flows through said tube and is discharged from said tube at said outlet adjacent to said cathode;
    electrical supply means connected to supply current to said cathode;
    gas supply means to supply gas to the interior of said cathode carrier tube through said supply inlet;
    an anode assembly having an interior chamber sized to receive said cathode tube therein in spaced relationship therewith;
    said anode assembly also including a gas exhaust port at one end thereof communicating with said interior chamber and through which gas is discharged from said tool for contacting live tissue to be incised and cauterized adjacent to said tool;
    said anode assembly further including first and second means at its other end, the first of which means engages the tool body and the second of which means engages coolant flow control means;
    said anode assembly further including an anode portion normally spaced from said cathode;
    means to bias said cathode to said normal position spaced from said anode;
    electrical supply means connected to supply current to said anode;
    coolant flow control means having an axial bore, said means receiving said anode assembly in said bore and in spaced relation thereto, said means being emplaced inside said tool body in spaced relation thereto with one end of said means extending adjacent the anode but in non-sealing relation therewith, and the other end of said means engaging the anode assembly in sealing relation therewith;

a coolant supply line to introduce a fluid inside said tool body in the chamber formed between said body and said coolant flow control means;

a coolant exhaust line to evacuate a fluid from the chamber formed between the exterior surface of the anode assembly and the bore of said coolant flow control means; and arc establishment means including a plunger normally extending inside said tool body and being actuatable from the exterior thereof so that upon depressing said plunger the cathode is moved from normal position into contacting relationship with the anode so that an arc is established upon release of said plunger to permit the cathode to move toward the normal position spaced from said anode.

6. A plasma arc scalpel comprising:

a tool body having an axial chamber extending therethrough and including a nozzle at one end and an aperture at the other end for assembly purposes;

a tubular anode assembly having an axial bore extending therethrough, said anode assembly including a first threaded end and a large end to threadably engage in sealing relationship the surface of said axial chamber in said tool body;

an anode threadably engaging said first threaded end of said anode assembly and having an axial interior chamber therein with said chamber having a nozzle communicating to the exterior of said anode and through the nozzle in said tool body and with said anode threadably engaging said anode assembly with said axial chamber in alignment with the axial bore of said anode assembly;

sealing means interposed between the nozzle of said anode and the tool body;

a cathode tube carrier for insertion inside the axial bore of said anode assembly;

insulative spacers to support said cathode carrier in spaced relationship with respect to said anode assembly;

a cathode secured to one end of said tube carrier with gas flow passages extending between the interior of said tube and the outer surface of said cathode, and said cathode normally extending toward said anode to define a predetermined gap sufficient to sustain an established electrical arc discharge when a preselected voltage is applied between the anode and cathode;

an anode shield tube threadably engaging in sealing relationship a portion of said anode assembly at one end and with the other end extending substantially adjacent said cathode, said shield defining a coolant flow path between the surface of the axial chamber of the tool body and the outside surface of said shield to a point substantially adjacent the anode, said anode shield also defining a coolant flow path between the inside surface of said shield tube and the outside surface of the anode assembly;

coolant inlet means to inject coolant at a point at the large end of the anode assembly between the tool body and the anode shield;

coolant outlet means to provide an outlet for coolant at a point at the large end of the anode assembly between the inside surface of the shield tube and the outside surface of the anode assembly;

biasing means interposed between the cathode tube carrier and the anode assembly normally urging the cathode away from contact with the anode;

plunger means extending outside the tool body to act upon the cathode carrier tube when depressed to urge the cathode toward contact with the anode; and electrical supply means including a wire connected to the anode assembly and another wire connected to the cathode carrier tube, whereby when sufficient voltage is supplied across the normal anode and cathode gap, and when a contact is established between said anode and cathode and the plunger means released, an arc is established and the inert gas flows through said cathode carrier tube past the cathode, through said arc and is ejected from the tool as a hot plasma through said nozzle in the anode.

\* \* \* \* \*